(12) United States Patent
Collier, Jr. et al.

(10) Patent No.: US 6,509,355 B1
(45) Date of Patent: Jan. 21, 2003

(54) TREATMENT OF DISORDERS OF THE OUTER RETINA

(75) Inventors: Robert J. Collier, Jr., Arlington, TX (US); Mark R. Hellberg, Arlington, TX (US); Michael A. Kapin, Arlington, TX (US); George E. Barnes, Arlington, TX (US); Michael L. Chandler, Crowley, TX (US)

(73) Assignee: Alcon Laboratories, Inc., Ft. Worth, TX (US)

(*) Notice: Subject to any disclaimer, the term of this patent is extended or adjusted under 35 U.S.C. 154(b) by 0 days.

(21) Appl. No.: 09/807,805

(22) PCT Filed: Oct. 20, 1999

(86) PCT No.: PCT/US99/24502

§ 371 (c)(1),
(2), (4) Date: Apr. 18, 2001

(87) PCT Pub. No.: WO00/24396

PCT Pub. Date: May 4, 2000

Related U.S. Application Data

(60) Provisional application No. 60/105,712, filed on Oct. 27, 1998.

(51) Int. Cl.$^7$ ............................................. A61K 31/445
(52) U.S. Cl. ..................................... 514/317; 514/912
(58) Field of Search ................................. 514/317, 912

(56) References Cited

U.S. PATENT DOCUMENTS

| | | |
|---|---|---|
| 4,690,931 A | 9/1987 | Wick et al. ................. 514/317 |
| 5,547,963 A | 8/1996 | Poindron et al. ............ 514/317 |
| 5,604,244 A | 2/1997 | DeSantis, Jr. et al. ....... 514/317 |
| 5,710,165 A | 1/1998 | Kapin et al. ................ 514/317 |

FOREIGN PATENT DOCUMENTS

| | | |
|---|---|---|
| WO | 97/09309 | 3/1997 |
| WO | 97/09310 | 3/1997 |

OTHER PUBLICATIONS

Young, Richard W., "Solar radiation and age–related macular degneration," *Sur. Ophthal.*, vol. 32(4):252–269, Jan.–Feb., 1988.

Bressler, et al., "Age–related macular degeneration," *Sur Ophthal*, vol. 32(6):375–413, May–Jun. 1988.

Curcio, et al., "Photoreceptor loss in age–related macular degeneration," *Invest Ophthal & Vis Sci*, vol. 37(7):1236–1249, Jun. 1996.

Tso, et al., "Apoptosis in human retinal degenerations," *Trans AM Ophthal Soc*, vol. 94, 411–431, 1996.

Marshall, et al., "Histopathology of ruby and argon laser lesions in monkey and human retina," *British Journal of Ophthalmology*, vol. 59:610–613, 1975.

Taylor, et al., "Long–term effects of visible light on the eye," *Arch Ophthal*, vol. 110:99–104, Jan. 1992.

Naash, et al., "Induced acceleration of photoreceptor degeneration in transgenic mice expressing mutant rhodopsin," *Invest Ophthal & Vis Sci.*, 1996, vol. 37(5):775–782, Apr. 1996.

Cruickshanks, et al., "Sunlight and age–related macular degeneration. The Beaver Dam eye study," *Archives of Ophthalmology*, vol. 111:514–518, 1993.

Faktorovich, et al., "Photoreceptor degeneration in inherited retinal dystrophy delayed by basic fibroblast . . . ," *Nature*, vol. 347:83–86, Sep. 6, 1990.

Li, et al., "Amelioration of photo injury in rat retina by ascorbic acid: A histopathologic study," *Invest Ophthal & Vis Sci*, vol. 26:1589–1598, Nov., 1985.

Organisciak, et al., "Protection by dimethylthiourea against retinal light damage in rats," *Invest Ophthal & Vis Sci*, vol. 33(5):1599–1609, Apr. 1992.

Lam, et al., "Amelioration of retinal photoic injury in albino rats by dimethylthiourea," *Arch Ophthal.* vol. 108, 1751–1757, 1990.

Kozaki, et al., "Light–induced retinal damage in pigmented rabbit—2. Effect of alpha–tocopherol," *Nippon Ganka Gakkai Zasshi*, vol. 98(10):948–954, Oct. 1994.

Rapp, et al., "Evaluation of retinal susceptibility to light damage in pigmented rats supplemented with beta–Carotene," *Cur Eye Res*, vol. 15, 219–223, 1995.

Li, et al., "Amelioration of retinal photic injury by a combination of flunarizine and dimethylthiourea," *Exp Eye Res*, vol. 56:71–78, 1993.

Edward, et al., "Amelioration of light–induced retinal degeneration by a calcium overload blocker," *Arch Ophthal*, vol. 109:554–562, Apr. 1991.

LaVail, et al., "Multiple growth factors, cytokines, and neurotrophins rescue photoreceptors from the damaging effects of constant light," *Proc Nat Acad Sci*, vol. 89:11249–11253, Dec. 1992.

Lam, et al., "Methylprednisolone therapy in laser injury of the retina," *Graefes Arch Clin Exp Ophthal.*, vol. 231:729–736, 1993.

Fu, et al., "Dexamethasone ameliorates retinal photic injury in albino rats," *Exp Eye Res*, vol. 54:583–594, 1992.

Lam, et al., ". . . ameliorates retinal photic injury in albino rats," *Cur Eye Res*, vol. 2:133–144, 1991.

Sabel, et al., "A behavioral model of excitotoxicity: retinal degeneration, loss of vision, and subsequent recovery after intraocular . . . ," *Exp Brain Res*, vol. 106:93–105, 1995.

Siliprandi, et al., "N–methyl–d–aspartate–induced neurotoxicity in the adult rat retina," *Vis Neurosci*, vol. 8:567–573, 1992.

(List continued on next page.)

Primary Examiner—Zohreh Fay
(74) Attorney, Agent, or Firm—Sally S. Yeager

(57) ABSTRACT

This invention is directed to the use of glutamate antagonists to treat the disorders of outer retina.

7 Claims, 3 Drawing Sheets

OTHER PUBLICATIONS

Gupta, et al., "Mannitol, dextromethorphan, and catalase minimize ischemic damage to retinal pigment . . . ," *Arch Ophthal*, vol. 111:384–388, Mar. 1993.

Solberg, et al., "MK–801 has neuroprotective and antiproliferative effects in retinal laser injury," *Invest Ophthal & Vis Sci*, vol. 38(7):1380–1389, Jun. 1997.

Carter, et al., "Ifenprodil and SL 82.0715 as cerebral anti-ischemic agents. III. Evidence for antagonistic . . . ," *Journal of Pharmacology and Experimental Therapeutic*, vol. 253(2):475–482, Aug. 1989.

Beart, et al., "Blockade by polyamine NMDA antagonists related to ifenprodil of NMDA–induced . . . ," *British Journal of Pharmacology*, vol. 114:1359–1364, 1995.

Chenard, et al., "Oxindole N–Methyl–D–aspartate (NMDA) antagonists," *Bioorganic & Medicinal Chemistry Letters*, vol. 13(1): 91–94, 1993.

Chenard, et al., "(1S, 2S)–1–(4–Hydroxyphenyl)–2–(4–hydroxy–4–phenylpiper idino)–1–propanol: A potent new . . . ," *Journal of Medicinal Chemistry*, vol. 38:3138–3145, 1995.

Butler, et al., "(3R,4S)–3–[4–(4–Fluorophenyl)–4–hydroxypiperidin–1–yl]chroman–4,7–diol: A conformatinally . . . ," *Journal of Medicinal Chemistry*, vol. 41, 1172–1184, 1998.

Chenard, et al., "Separation of a1 adrenergic and N–methyl–d–aspartate antagonist activity in a series . . . ," *Journal of Medicinal Chemistry*, vol. 34, 3085–3090, 1994.

Avenet, et al., "Antagonist properties of eliprodil and other NMDA receptor antagonists at rat NR1A/NR2A . . . ," *Neuroscience Letters*, vol. 223: 133–136, 1997.

Boeckman, et al., "Pharmacological properties of acquired excitotoxicity in chinese hamster ovary cells . . . ," *Journal of Pharmacology and Experimental Therapeutic*, vol. 279(2):515–523, 1996.

Bath, et al., "The effects of ifenprodil and eliprodil on voltage–dependent $Ca^{2+}$ channels and in gerbil . . . ," *European Journal of Pharmacology*, vol. 299:103–112, 1996.

Biton, et al., "The NMDA receptor antagonist eliprodil (SL 82.0715) blocks voltage–operated . . . ," *European Journal of Pharmacology*, vol. 257:297–301, 1994.

Green, et al., "Pathologic findings of photic retinopathy in the human eye," *American Journal of Ophthalmology*, vol. 112:520–27, 1991.

Lambiase, et al., "Nerve growth factor delays retinal degeneration in C3H mice," *Graefes Arch Clin and Exp Ophthal*, vol. 234: S96–S100, 1996.

Scatton, et al., "Eliprodil Hydrochloride," *Drugs of the Future*, vol. 19(10):905–909, 1994.

Shahinfar, et.al., "A pathologic study of photoreceptor cell death in retinal photic injury," *Current Eye Research*, vol. 10(1):47–59, 1991.

Abler, et.al., "Photic injury triggers apoptosis of photoreceptor cells," *Investigative Ophthalmology & Visual Science*, vol. 35(Suppl):1517, 1994.

Chang, et al., "Apoptotic photoreceptor cell death after traumatic retinal detachment in humans," *Archives of Ophthalmology*, vol. 113:880–886, 1995.

Portera–Cailliau, et al., "Apoptotic photoreceptor cell death in mouse models of retinitis pigmentosa," *Proceedings of National Academy of Science (U.S.A.)*, vol. 91:974–978, 1994.

Buchi, Ernst R., Cell death in the rat retina after a pressure–induced ischaemia–reperfusion insult: an . . . , *Experimental Eye Research*, vol. 55:605–613, 1992.

Quigley, et al., "Retinal ganglion cell death in experimental glaucoma and after axotomy occurs by apoptosis," *Investigative Ophthalmology & Visual Science*, vol. 36(5):774–786, 1995.

Zigman, et al., "The response of mouse ocular tissues to continuous near–UV light exposure," *Investigative Ophthalmology & Visual Science*, vol. 14:710–713, 1975.

Noell, et al., "Retinal damage by light in rats," *Invest. Ophthal & Vis Sci.*, vol. 5(5):450–472, Oct., 1966.

Kuwabara, et al., "Retinal damage by visible light: An electron microscopic study," *Archives of Ophthalmology*, vol. 79:69–78, 1968.

LaVail, M. M., "Survival of some photoreceptor cells in albino rats following long–term exposure to continuous light," *Investigative Ophthalmology & Visual Science*, vol. 15(1):64–70, 1976.

Lawwill, T., "Effects of prolonged exposure of rabbit retina to low–intensity light," *Investigative Ophthalmology & Visual Science*, vol. 12(1):45–51, 1973.

Collier, et al., "Comparison of retinal photochemical lesions after exposure to Near–UV or short–. . . ," *Inherited and Environmentally induced Retinal Degenerations*, pp. 569–575, 1989.

Collier, et al., "Temporal sequence of changes to the ray squirrel retina after near–UV exposure," *Investigative Ophthalmology & Visual Science*, vol. 30(4):631–637, 1989.

Tso, M., "Photic maculopathy in rhesus monkey. A light and electron microscopic study," *Investigative Ophthalmology & Visual Science*, vol. 12:17–34, 1973.

Ham, et al., The nature of retinal radiation damage: dependence on wavelength, power level and . . . , *Vision Research*, vol. 20:1105–1111, 1980.

Sperling, et al., "Differential spectral photic damage to primate cones," *Vision Research*, vol. 20:1117–1125, 1980.

Sykes, et al., "Damage to the monkey retina by broad spectrum fluorescent light," *Investigative Ophthalmology & Visual Science*, vol. 20:425–434, 1981.

Lawwill, T., "Three major pathologic processes caused by light in the primate retina: A search for mechanisms," *Transactions of the American Ophthalmology Society*, vol. 80:517–579, 1982.

* Significantly higher amplitude compared to vehicle (p<0.05).

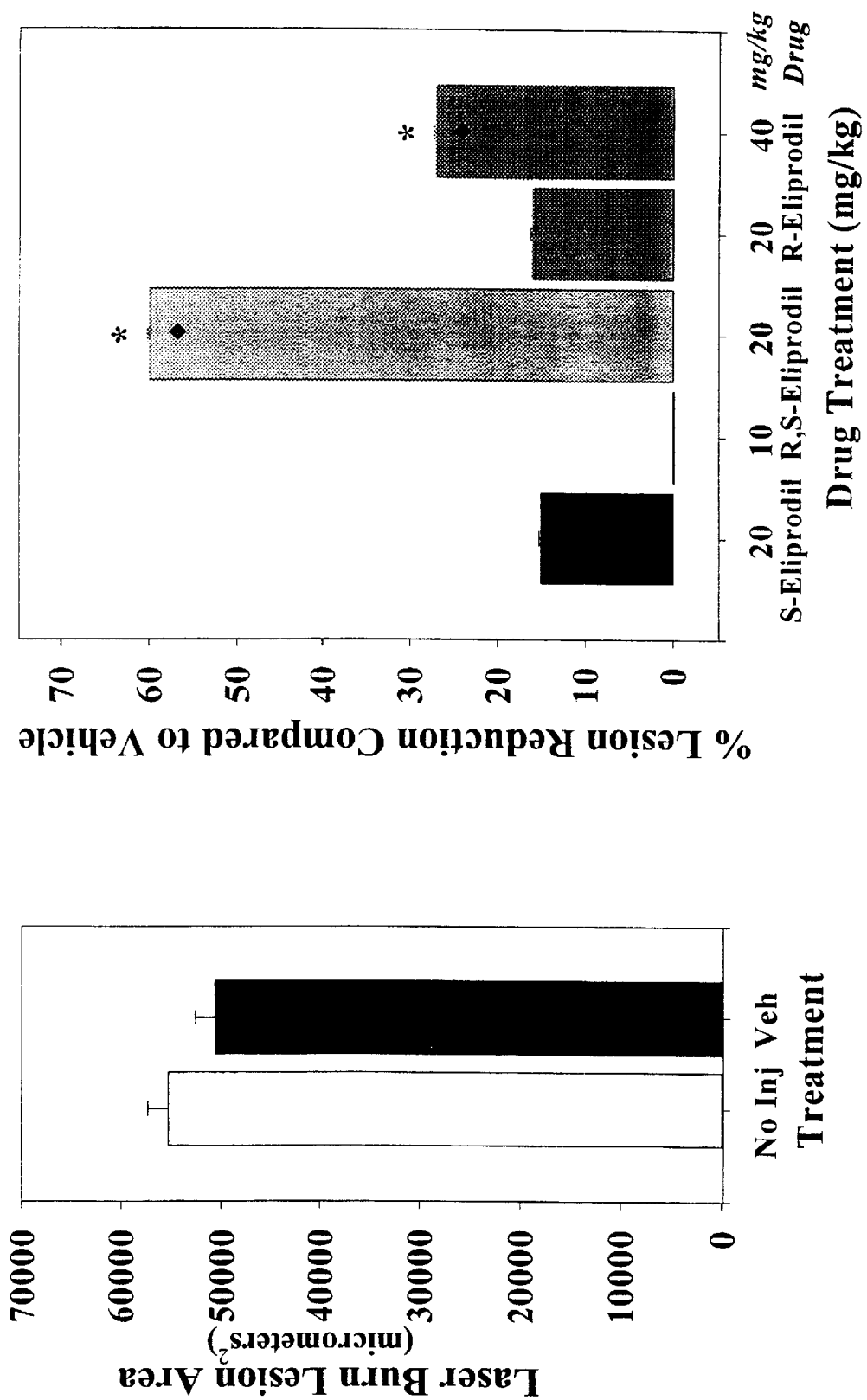

TREATMENT OF DISORDERS OF THE OUTER RETINA

This application claims priority from PCT/US99/24502, filed on Oct. 20, 1999, which claims priority from U.S. Serial No. 60/105,712, filed on Oct. 27, 1998.

This invention is directed to the use of glutamate antagonists to treat disorders of the outer retina.

BACKGROUND OF THE INVENTION

The pathogenesis of retinal degenerative diseases such as age-related macular degeneration (ARMD) and retinitis pigmentosa (RP) is multifaceted and can be triggered by environmental factors in those who are genetically predisposed. One such environmental factor, light exposure, has been identified as a contributing factor to the progression of retinal degenerative disorders such as ARMD (*Sur Ophthal*, 1988, 32. 252–269). Photo-oxidative stress leading to light damage to retinal cells has been shown to be a useful model for studying retinal degenerative diseases for the following reasons: damage is primarily to the photoreceptors and retinal pigment epithelium of the outer retina (*Invest Ophthal & Vis Sci*, 1966, 5, 450–472; *Sur Ophthal*, 1988, 32, 375–413, *Invest Ophthal & Vis Sci*, 1996, 37, 1236–1249); they share a common mechanism of cell death, apoptosis (*Trans AM Ophthal Soc*, 1996, 94, 411–430, *Res Commun Mol Paihol Pharmacol*, 1996, 92, 177–189); light has been implicated as an environmental risk factor for progression of ARMD and RP (*Arch Ophthal*, 1992, 110, 99–104; *Invest Ophihal & Vis Sci*, 1996, 37, 775–782); and therapeutic interventions which inhibit photo-oxidative injury have also been shown to be effective in animal models of heredodegenerative retinal disease (*Proc Nat Acad Sci*, 1992, 89, 11249–11253; *Nature*, 25 1990, 347, 83–86).

A number of different classes of compounds have been reported to minimize retinal photic injury in various animal models: antioxidants, such as, ascorbate (*Invest Ophthal & Vis Sci*, 1985, 26, 1589–1598), dimethylthiourea (*Invest Ophthal & Vis Sci*, 30 1992, 33, 450–472; *Arch Ophthal*, 1990, 108, 1751–1752), α-tocopherol (*Nippon Ganka Gakkai Zasshi*, 1994, 98, 948–954), and β-carotene (*Cur Eye Res*, 1995, 15, 219–232); calcium antagonists, such as, flunarizine, (*Exp Eye Res*, 1993, 56, 71–78, *Arch Ophthal*, 1992, 109, 554–622); growth factors, such as, basic-fibroblast growth factor, brain derived nerve factor, ciliary neurotrophic factor, and interleukin-1-β (*Proc Nat Acad Sci*, 1992, 89, 11249–11253); glucocorticoids, such as, methylprednisolone (*Graefes Arch Clin Exp Ophihal*, 1993, 231, 729–736), dexamethasone (*Exp Eye Res*, 1992, 54, 583–594); and iron chelators, such as, desferrioxamine (*Cur Eye Res*, 1991, 2, 133–144).

To date, excitatory amino acid antagonists have not been evaluated in models of outer retinal degeneration as several studies have demonstrated that principally inner retinal cells are sensitive to excitatory amino acid toxicity, while exposure to excitatory to amino acids has no effect on outer retina photoreceptors and retinal pigment epithelial (RPE) cells (*Exp Brain Res*, 1995, 106, 93–105: *Vis Neurosci*, 1992, 8, 567–573). However, when tested in a model of mechanical stress induced ischemia reperfusion, inner retina function and RPE function were moderately protected by dextromethorphan treatment but no significant protective effect was measured for outer retina function (*Arch Ophihal*, 1993, 111, 384–388). Similarly, MK-801 was found to be minimally effective at 60 days in preventing the spread of laser induced thermal burns to the retina, but did not significantly prevent photoreceptor loss when evaluated at 3 and 20 days post laser exposure (*Invest Ophthal & Vis Sci*, 1997, 38, 1380–1389).

A series of N-methyl-D-aspartate (NMDA) antagonists including eliprodil, ifenprodil, CP-101,606, tibalosine, 2309BT, 840S, and related structural analogs are effective neuroprotectants that are believed to modulate excitatory amino acid toxicity by interacting at the polyamine binding site of the NMDA receptor (*Journal of Pharmacology and Experimental Therapeutic*, 1990, 253, 475–482, *British Journal of Pharmacology*, 1995, 114, 1359–64, *Bioorganic & Medicinal Chemistry Letters*, 1993, 13, 91–94, *Journal of Medicinal Chemistry*, 1995, 38, 313845, *Journal of Medicinal Chemistry*, 1998, 41, 1172–1184, *Journal of Medicinal Chemistry*, 1991, 34, 3085–3090, WO 97/09309 Synthélabo, WO 97/09310 Synthélabo). More specifically ifenprodil, eliprodil, and CP-101,606 have recently been shown to preferentially block to the NR1A/NR2B subtype of the polyamine binding site of the NMDA receptor (*Neuroscience Letters*, 1997, 223, 133–136, *Journal of Pharmacology and Experimental Therapeutic*, 1996, 279, 515–523). The selective interaction of the compounds with the polyamine site of the NMDA receptor subunit is believed to be responsible at least in part for both the neuroprotective activity and the relatively favorable side effects profile of this class of compounds when compared to NMDA antagonists that act at other sites on the NMDA receptor, such as MK-801 and PCP.

In addition to having activity as NMDA antagonists, certain compounds, such as, eliprodil and ifenprodil, have calcium antagonist activity at both the calcium, N, P, and L channels. (*European Journal of Pharmacology*, 1996, 299, 103–1 12, *European Journal of Pharmacology*, 1994, 257, 297–301). Other calcium antagonists, such as, flunarizine, have also been shown to be protective in light induced damage models (*Exp Eye Res*, 1993, 56, 71–78; *Arch Ophthal*, 109, 1991, 554–62).

BRIEF DESCRIPTION OF THE DRAWINGS

FIG. 3 shows the prevention of collateral retinal laser burn damage by eliprodil and its enantiomers.

Figure 1:
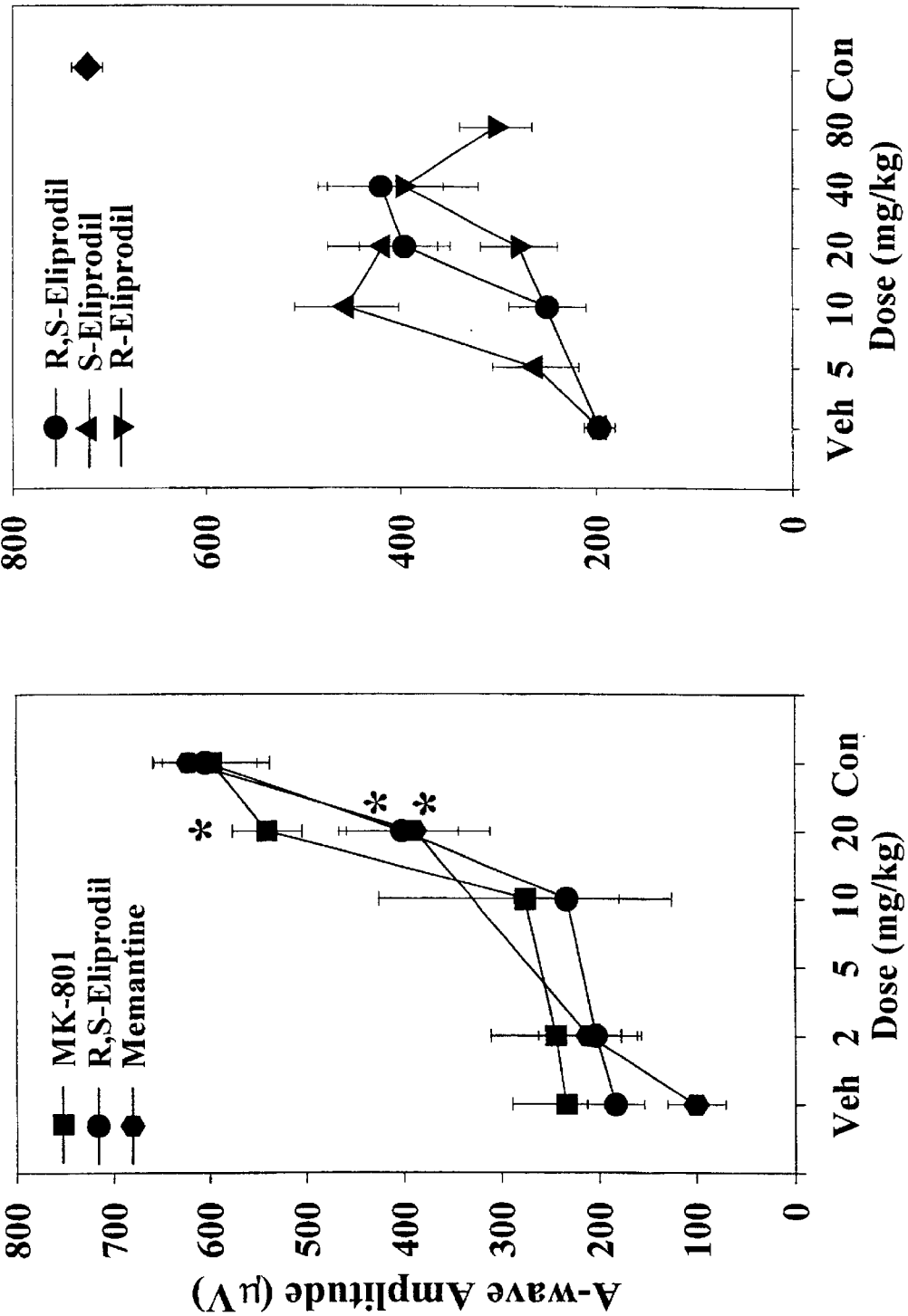
FIG. 1 shows the prevention of photic retinopathy by eliprodil and other glutamate agonists.

The present invention is directed to glutamate antagonists which have been discovered to be useful in treating disorders of the outer retina, particularly: age-related macular degeneration; retinitis pigmentosa and other forms of heredodegenerative retinal disease; retinal detachment and tears; macular pucker; ischemia affecting the outer retina; damage associated with laser therapy (grid, focal and panretinal) including photodynamic therapy (PDT); trauma; surgical (retinal translocation, subretinal surgery or vitrectomy) or light induced iatrogenic retinopathy; and preservation of retinal transplants. As used herein the outer retina includes the RPE, photoreceptors, Muller cells (to the extent they are found in the outer retina), and the outer plexiform layer. The compounds are formulated for systemic or local ocular delivery.

In our light damage paradigms, antioxidants were either ineffective (alpha-tocopherol) or marginally effective at high doses (ascorbate, vitamin E analogs). Similarly, some calcium antagonists (flunarizine, nicardipine) were moderately effective while others (nifedipine, nimodipine, barnidipine, verapamil, lidoflazine, prenylamine lactate, amiloride) had no effect in preventing light induced functional or morphological changes. However, it has been discovered that NMDA antagonists are effective in treating disorders of the outer retina.

As used herein the term glutamate antagonist means antagonist of the NMDA receptor channel complex. NMDA receptor antagonists include channel blockers (agents that operate uncompetitively to block the NMDA receptor channel); receptor antagonists (agents that compete with NMDA or glutamate at the NMDA binding site; agents acting at the glycine coagonist site or any of several modulation sites (e.g., zinc, magnesiums, redox, or polyamine sites). Disorders of the outer retina encompasses acute and chronic In environmentally induced (trauma, ischemia, photo-oxidative stress) degenerative conditions of the outer retina (retinal pigment epithelial cells "RPE cells") in genetically predisposed individuals. This would include, but not be limited to, age-related macular degeneration, retinitis pigmentosa and other forms of heredodegenerative retinal disease, retinal detachment, tears, macular pucker, ischemia affecting the outer retina, damage associated with laser therapy (grid, focal and panretinal) including photodynarnic therapy (PDT), trauma, surgical (retinal translocation, subretinal surgery or vitrectomy) or light induced iatrogenic retinopathy and preservation of retinal transplants. Preferred glutamate antagonists inhibit excitotoxicity by binding at the polyamine site and have calcium antagonist and/or sodium antagonist, and/or neurotrophic activity. The glutamate antagonists which have been found to be particularly effective have the following structure.

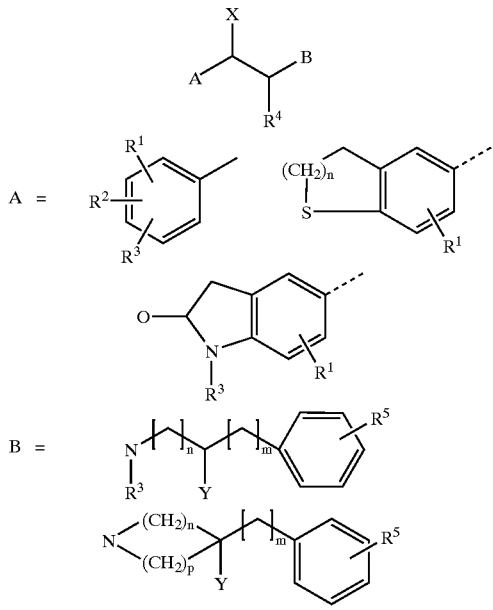

Y,X=OH, H
m=0–3
n, p=1,2
$R^1$=H, halogen, trifluoromethyl, C1–4 alkyl, OH, C1–4 alkoxy, benzyloxy, C1–16 alkanoyloxy, benzoyloxy or when $R^2$=OH or methoxy in the 4-position and $R^3$=H then
$R^1$=hyroxymethyl, carbamoyl, or C1–4 alkoxycarbonyl;
$R^2$=H, halogen, C1–4 alkyl, OH, C1–4 alkoxyl;
$R^3$, $R^4$=H, C1–4 alkyl; and
$R^5$=H, halogen, trifluoromethyl, C1–4 alkyl, OH, C1–4 alkoxy, benzyloxy, C1–16 alkanoyloxy, benzoyloxy.

These compounds include all isomers and pharmaceutically acceptable salts.

In the preferred embodiments the glutamate antagonist is 2-[4-(4-fluorobenzyl)-piperidino]-1-(4-chlorophenyl) ethanol (eliprodil) and/or its R or S isomers.

Certain compounds of this invention have also been shown to have a neurotrophic effect see U.S. Pat. No. 5,547,963). Since it has been shown that nerve growvth factor inhibits retinal degeneration in a mouse strain genetically predisposed to retinal degeneration (*Graefes Arch Clin and Exp Ophthal,* 1996, 234 *supplement* 1, S96–100) the neurotrophic activity of the compounds of this invention may provide an additional therapeutic effect.

In general, for degenerative diseases, the compounds of this invention are administered orally with daily dosage of these compounds ranging between 0.01 and 500 milligrams. The preferred total daily dose ranges between 1 and 100 milligrams. Non-oral administration, such as, intravitreal, topical ocular, transdermnal patch, parenteral, intraocular, subconjunctival, or retrobulbar injection, iontophoresis or slow release biodegradable polymers or liposomes may require an adjustment of the total daily dose necessary to provide a therapeutically effective amount of the compound. The compounds can also be delivered in ocular irrigating solutions used during surgery see U.S. Pat. No. 5604,244 for irrigating solution formulations. This patent is herein incorporated by reference. Concentrations should range from 0.001 $\mu$M to 10 $\mu$M, preferably 0.01 $\mu$m to 5 $\mu$M.

The compounds can be incorporated into various types of ophthalmic formulations for topical delivery to the eye. They may be combined with ophthalmologically acceptable preservatives, surfactants, viscosity enhancers, penetration enhancers, buffers, sodium chloride, and water to form aqueous, sterile ophthalmic suspensions or solutions. Ophthalmic solution formulations may be prepared by dissolving the compound in a physiologically acceptable isotonic aqueous buffer. Further, the ophthalmic solution may include an ophthalmologically acceptable surfactant to assist in dissolving the compound. The ophthalmic solutions may contain a thickener, such as, hydroxymethylcellulose, hydroxyethylcellulose, hydroxypropylmethylcellulose, methylcellulose, polyvinyl-pyrrolidone, or the like, to improve the retention of the formulation in the conjunctival sac. In order to prepare sterile ophthalmic ointment formulations, the active ingredient is combined with a preservative in an appropriate vehicle, such as, mineral oil, liquid lanolin, or white petrolatum. Sterile ophthalmic gel formulations may be prepared by suspending the active ingredient in a hydrophilic base prepared from the combination of, for example, carbopol-940, or the like, according to the published formulations for analogous ophthalmic preparations; preservatives and tonicity agents can be incorporated.

If dosed topically, the compounds are preferably formulated as topical ophthalmic suspensions or solutions, with a pH of about 4 to 8. The compounds will normally be contained in these formulations in an amount 0.001% to 5% by weight, but preferably in an amount of 0.01% to 2% by weight. Thus, for topical presentation, 1 to 2 drops of these formulations would be delivered to the surface of the eye 1 to 4 times per day according to the routine discretion of a skilled clinician.

The preferred compound, eliprodil (or its R or S isomers), is orally bioavailable, demonstrates a low incidence of adverse effects upon administration, and effectively crosses the blood-brain barrier (*Drugs of the Future,* 1994, 19, 905–909) indicating that effective concentrations are expected in the target tissue, the retina. The compound is described in U.S. Pat. No. 4,690,931. the contents of which are incorporated herein by reference.

Eliprodil was evaluated in our light induced damage paradigm, a model of retinal degenerative diseases such as retinitis pigmentosa and age-related macular degeneration. Unexpectedly eliprodil, an excitatory amino acid antagonist, demonstrated marked potency and efficacy as a cytoprotective agent. Both photoreceptor and RPE cells were completely protected from light induced functional changes and morphologic lesions.

EXAMPLE 1

Photo-oxidative Induced Retinopathy

Photic retinopathy results from excessive excitation of the retinal pigment epithelium and neuroretina by absorption of visible or near ultraviolet radiation. Lesion severity is dependent upon wavelength, irradiance, exposure duration, species, ocular pigmentation, and age. Damage may result from peroxidation of cellular membranes, inactivation of mitochondrial enzymes such as cytochrome oxidase, or increased intracellular calcium. Cellular damage resulting from photo-oxidative stress leads to cell death by apoptosis, (Shahinfar, S., Edward. D. P. and Tso, M. O. (1991), A pathologic study of photoreceptor cell death in retinal photic injury. *Current Eye Research,* 10:47–59: Abler, A. S., Chang, C. J., Fu, J. and Tso, M. O. (1994), Photic injury triggers apoptosis of photoreceptor cells. *Investigative Ophthalmology & Visual Science,* 35(Suppl):1517). Oxidative stress induced apoptosis has been implicated as a cause of many ocular pathologies, including, iatrogenic retinopathy, macular degeneration, retinitis pigmentosa and other forms of heredodegenerative disease, ischemic retinopathy, retinal tears, retinal detachment, glaucoma and retinal neovascularization (Chang, C. J., Lai, W. W., Edward, D. P. and Tso, M. O. (1995), Apoptotic photoreceptor cell death after traumatic retinal detachment in humans, *Archives of Ophthalmology,* 113:880–886: Portera-Cailliau, C., Sung, C. H., Nathans, J. and Adler, R. (1994), Apoptotic photoreceptor cell death in mouse models of retinitis pigmentosa, *Proceedings of National Academy of Science* (U.S.A.), 91:974–978; Buchi, E. R. (1992), Cell death in the rat retina after a pressure-induced ischaemia-reperfusion insult: an electron microscopic study. I. Ganglion cell layer and inner nuclear layer, *Experimental Eye Research,* 55:605–613; Quigley, H. A., Nickells. R. W., Kerrigan, L. A., Pease, M. E., Thibault, D. J. and Zack, D. J. (1995), Retinal ganglion cell death in experimental glaucoma and after axotomy occurs by apoptosis, *Investigative Ophthalmology & Visual Science,* 36:774–786). Photic induced retinal damage has been observed in mice (Zigman, S., Groff, J., Yulo, T. and Vaughan, T. (1975), The response of mouse ocular tissues to continuous near-UV light exposure. *Investigative Ophthalmology & Visual Science,* 14:710–713), rats (Noell, W. K., Walker, V. S., Kang, B. S., and Berman, S. (1966), Retinal damage by light in rats, *Investigative Ophthalmology and Visual Science,* 5:450–473; Kuwabara, T. and Gorn, R. A. (1968), Retinal damage by visible light: An electron microscopic study, *Archives of Ophthalmology,* 79:69–78; LaVail, M. M. (1976), Survival of some photoreceptor cells in albino rats following long-term exposure to continuous light, *Investigative Ophthalmology & Visual Science,* 15:64–70), rabbit (Lawwill, T. (1973), Effects of prolonged exposure of rabbit retina to low-intensity light, *Investigative Ophthalmology & Visual Science,* 12:45–51), squirrel (Collier, R. J. and Zigman, S. (1989), Comparison of retinal photochemical lesions after exposure to Near-UV or short-wavelength visible radiation, In M. M. LaVail, R. E. Anderson, and J. G. Hollyfield (Eds.), *Inherited and Environmentally induced Retinal Degenerations.* Alan R. Liss, Inc., New York; Collier, R., W. Waldron and Zigman, S. (1989), Temporal sequence of changes to the gray squirrel retina after near-UV exposure, *Investigative Ophthalmology & Visual Science,* 30:631–637), non-human primates (Tso, M. O. M. (1973), Photic maculopathy in rhesus monkey. A light and electron microscopic study. *Investigative Ophthalmology & Visual Science,* 12:17–34; Ham, W. T., Jr., Ruffolo, J. J., Jr., Mueller, H. A. and Guerry, D., III. (1980), The nature of retinal radiation damage: dependence on wavelength, power level and exposure time, *Vision Research,* 20:1105–1111; Sperling, H. G., Johnson, C. and Harwerth, R. S. (1980), Differential spectral photic damage to primate cones, *Vision Research,* 20:1117–1125: Sykes, S. M., Robison, W. G., Jr., Waxler, M. and Kuwabara, T. (1981), Damage to the monkey retina by broad spectrum fluorescent light, *Investigative Ophthalmology & Visual Science,* 20:425–434; Lawwill, T. (1982), Three major pathologic processes caused by light in the primate retina: A search for mechanisms, *Transactions of the American Ophthalmology Society,* 80:517–577), and man (Marshall, J. Hamilton, A. M. and Bird, A. C. (1975), Histopathology of ruby and argon laser lesions in monkey and human retina, *British Journal of Ophthalmology,* 59:610–630; Green, W. R. and Robertson, D. M. (1991), Pathologic findings of photic retinopathy in the human eye. *American Journal of Ophthalmology,* 112:520–27). In man, chronic exposure to environmental radiation has also been implicated as a risk factor for age-related macular degeneration (Young, R. W. (1988), Solar radiation and age-related macular degeneration, *Survey of Ophthalmology,* 32:252–269; Taylor, H. R., West, S., Munoz, B., Rosenthal, F. S., Bressler. S. B. and Bressler, N. M. (1992), The long-term effects of visible light on the eye, *Archives of Ophthalmology,* 110:99–104; Cruickshanks, K. J., Klein, R. and Klein, E. K. (1993), Sunlight and age-related macular degeneration. The Beaver Dam Eye Study, *Archives of Ophthalmology,* 111:514–518).

To determine if eliprodil and other glutamate antagonists can rescue retinal cells from photo-oxidative insult, male Sprague Dawley rats were randomly assigned to drug or vehicle experimental groups. In Experiment 1, rats were dosed with various glutamate antagonists, including: MK-801; eliprodil; and memantine and in Experiment 2, the potency of eliprodil was compared to the potency of its isomers. In both experiments, rats received three intra peritoneal (IP) injections of either vehicle or drug at 48, 24, and 0 hours prior to a 6-hour light exposure to spectrally filtered blue light (~220 fc). Control rats were housed in their home cage under normal cyclic light exposure. The electroretinogram (ERG) is a non-invasive clinical measurement of the electrical response of the eye to a flash of light. The a-wave and b-wave are two components of the ERG that are diagnostic of retinal function. The a-wave reflects outer retina function and is generated by interactions between photoreceptor and pigment epithelial cells while the b-wave reflects inner retina function, particularly Muller cells. The ERG was recorded after a five day recovery period from dark-adapted anesthetized rats (Ketamine-HCl, 75 mg/Kg; Xylazine, 6 mg/Kg). The eyes' electrical response to a flash of light was elicited by viewing a ganzfeld. ERGs to a series of light flashes increasing in intensity were digitized to analyze temporal characteristics of the waveform and response voltage-log intensity (VlogI) relationship.

Results

Effect of blue-light exposure on vehicle dosed rats: Blue-light exposure for 6 hours resulted in a significant diminution of the ERG response amplitude (ANOVA, $p<0.001$; Bonferroni t-test, $p<0.05$) compared to controls when measured after a 5-day recovery period (FIG. 1-A). Maximum a-wave and b-wave amplitudes were reduced more than 70% in vehicle-dosed rats compared to controls. In addition, threshold responses were lower and evoked at brighter flash intensities.

Experiment 1 Prevention of Photic Retiniopathiy with Glutamate Antagonists

Rats dosed with MK-801, eliprodil or memantine showed dose-dependent protection of outer and inner retina function against this photo-oxidative induced retinopathy 1.) MK-801. MK-801 provided significant protection of outer and inner retina function against light induced retinal degeneration in rats dosed with 20 mg/kg. Further, response amplitudes, waveforms, and threshold responses were not significantly different than control. Maximum a-wave response amplitudes averaged 734.05 $\mu$V (SEM=36.79 $\mu$V) from controls and 537.93 $\mu$V (SEM=34.42 $\mu$V) from 20 mg/kg dosed rats (See FIG. 1-A). Similarly, maximum b-wave response amplitudes were not significantly different and averaged 1807 $\mu$V (SEM=74.32 $\mu$V) from controls and 1449.77 $\mu$V (SEM=68.12 $\mu$V) from MK-801 dosed rats. No significant protection of retinal function was measured in rats dosed with MK-801 at doses of 2 or 10 mg/kg.

2.) Eliprodil. Significant preservation of retinal function was also measured in cliprodil (racemic mixture) dosed rats (20 mg/kg) compared to vehicles (FIG. 1-A). The ERG a- and b-wave were 57% and 53% of normal and 2.4 and 2.2 fold higher than vehicle dosed rats, respectively. ERGs recorded from rats dosed with eliprodil (2 or 10 mg/kg) were not significantly different than vehicles and approximately 32% of normal.

3.) Memantine. As shown in FIG. 1-A, no significant protection of outer and inner retina function was measured in memantine (2 mg/kg) dosed rats. Memantine provided significant protection of outer and inner retina function against light induced retinal degeneration in rats dosed with 20 mg/kg compared to vehicle dosed rats. However, ERG responses were significantly lower than normal in rats dosed with 20 mg/kg.

Experiment 2: Comparison of Eliprodil with the R and S Isomer

1.) Eliprodil. Eliprodil (racemic) provided significant protection of outer and inner retina function against light induced retinal degeneration in rats dosed with 20 and 40 mg/kg (FIG. 1-B). Maximum a-wave response amplitudes in eliprodil dosed rats with 20 and 40 mg/kg were 2.4 and 2.25 fold higher, respectively, than vehicle dosed rats. After a 5-day recovery period, maximum a-wave response amplitudes averaged 395.82 $\mu$V (SEM=46.4 $\mu$V) from 20 mg/kg dosed rats and 419.85 $\mu$V (SEM=63.88 $\mu$V) from 40 mg/kg dosed rats. No significant difference in retinal function was detected between either dose group and these amplitudes were approximately 60% of normal.

2.) R-eliprodil. As seen in FIG. 1-B, R-eliprodil was two-fold less potent than eliprodil (racemic). No significant protection of outer an d inner retina function was measured after a 5-day recovery period in rats dosed with R-eliprodil at 20 mg/kg. Maximum a- and b-wave responses were 38% and 36% of normal, respectively. However, R-eliprodil did provide significant protection of outer and inner retina function against light induced retinal degeneration in rats dosed with 40 mg/kg (FIG. 1-B). Response amplitudes were about 2 fold higher than vehicle dosed rats and 50% of normal. Maximum a- and b-wave response amplitudes averaged 397.25 $\mu$V (SEM=77.14 $\mu$V) and 812.87 $\mu$V (SEM=160.13 $\mu$V), respectively. No significant retinal protection was measured in rats dosed with the highest dose of R-eliprodil. 80 mg/kg. Maximum a- and b-wave responses were approximately 40% of normal.

3.) S-eliprodil. No significant difference in ERG response amplitude was measured between S-eliprodil (5 mg/kg) dosed rats compared to vehicle dosed rats. However, as seen in FIG. 1-B, S-eliprodil was two-fold more potent than eliprodil (racemic). Significant protection of outer and inner retina function was measured after a 5-day recovery period in rats dosed with S-eliprodil as low as 10 mg/kg compared to vehicles. Maximum a- and b-wave responses were 64% and 76% of normal, respectively. Significant protection of outer and inner retina function against light induced retinal degeneration compared to vehicle dosed rats was also measured in rats dosed with 20 mg/kg. Response amplitudes were about 2 fold higher than vehicle dosed rats and approximately 62% of normal after a 5-day recovery period. Maximum a- and b-wave response amplitudes averaged 418.04 $\mu$V (SEM=56.18 $\mu$V) and 1015.95 $\mu$V (SEM=141.49 $\mu$V), respectively.

SUMMARY

All glutamate antagonists evaluated from this series of compounds provided significant rescue of RPE and photoreceptor cells in this photic induced retinopathy model. Complete protection was measured in MK-801 dosed rats. The S-enantiomer was the most potent retinoprotective agent in this series of glutamate antagonists.

EXAMPLE 2

Retinal Laser Burn Spread Damage

The eye is exposed to high-energy laser radiation during the performance of retinal photocoagulation therapy (grid, focal and panretinal) or during photodynamic therapy. This type of therapy is often employed during treatment of choroidal neovascularization, proliferative stages of diabetic retinopathy, retinopathy of prematurity, or to repair retinal holes or detachrnents. Associated with this laser therapy is tissue destruction leading to vision deterioration. The Macular Photocoagulation Study found that 20% of the eyes treated for subfoveal macular choroidal neovascularizations (CNV) and 18% of the eyes treated for juxtafoveal CNV suffered severe visual loss of six or more lines as a direct result of laser treatment. It is believed that this vision loss results directly from the expansion of the laser-induced lesion to surrounding normal neurosensory retina and RPE. Singlet oxygen and other reactive oxygen species as well as cytokines are generated in the area of the laser burn and thought to migrate laterally to cause collateral retinal damage. Retinal morphology changes in this area are similar to changes in our photo-oxidative retinopathy paradigm.

The objective of this study was to quantitate change in laser burn size in vehicle dosed or eliprodil dosed rats to determine if therapeutic agents could minimize laser burn spread damage. Pigmented Long Evans rats were randomly assigned to control, vehicle or drug dosed groups. Rats were pre dosed (IP) 64, 48, 24, and 2 hours before lasering and 3, 19 and 25 hours after receiving 2 to 4 laser burns from an argon laser (spot size 200-microns, power intensity=100 mW, and exposure duration=0.1 seconds). After a 48-hour recovery period, eyes were fixed, dehydrated, and embedded in plastic resin. Histological assessment of laser burns was performed by flatmounting the retina and sectioning the tissue in a plane tangential to the nerve fiber layer. Using this technique, the lesion area in the outer nuclear layer could be calculated using an image analysis system.

Results

Figure 2:
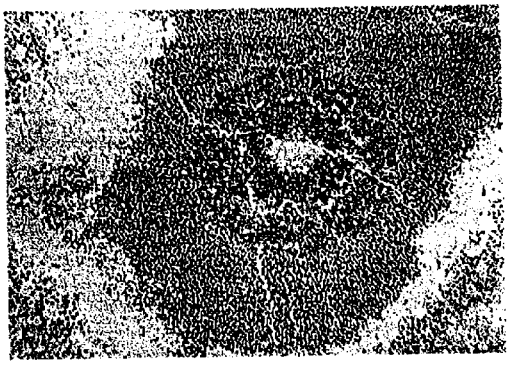
FIG. 2 shows protection of the retina from collateral damage due to laser treatment.
Figure 2:
Figure 2:
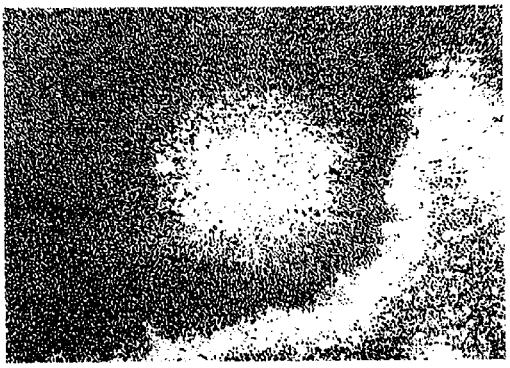
Figure 2:
Figure 2:
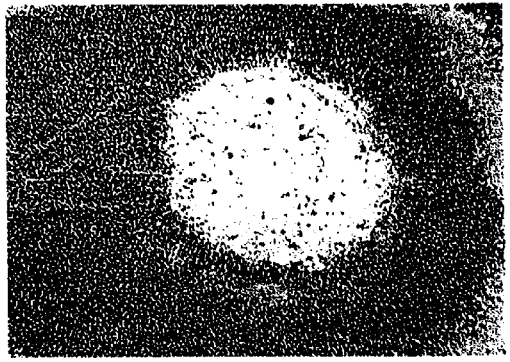

Histological assessment of retinal burns 48 hours after laser exposure showed that lesions were normally confined to the choriocapillaris, retinal pigment epithelium and outer retina. The laser burn center was marked by; complete closure of all capillaries, arterioles and venuoles; perforation of Bruch's membrane; pyknosis and necrosis of all photoreceptor nuclei; and destruction of inner and outer segments. Spread of the lesion into peripheral retina consisted of shortening of outer segments, inner segment swelling, clumping of melanin granules in the RPE and choroid, and vacuolization of the RPE. In control and vehicle-dosed eyes, laser burn areas averaged 50,627.07 and 55,243.65 $\mu^2$, respectively (FIGS. 2, 3).

1.) Eliprodil. Treatment with eliprodil (racemic) significantly reduced the retinal burn area approximately 60% (FIGS. 2, 3) compared to vehicle. The average burn area in eliprodil dosed rats was 22,406 $\mu^2$ (SEM= 3559.3 $\mu^2$) No reduction in laser lesion burn size was measured in rats dosed with 10 mg/kg. Laser burn lesion areas averaged 55,411.67 $\mu^2$ (SEM=2555.47 $\mu^2$) in this group of rats.

2.) R-eliprodil. Dosing with R-eliprodil (40 mg/kg) resulted in lesion areas that were 28% smaller than lesions in vehicle dosed rats. Laser burn lesion areas in R-eliprodil dosed rats averaged 36,016 $\mu^2$ (SEM= 4779.49 $\mu^2$) and were significantly different than vehicle dosed or non-injected lesions (FIG. 3). Dosing with R-eliprodil (20 mg/kg) resulted in laser lesion areas that were 16% smaller than lesions measured in vehicle dosed rats but were not significantly different.

3.) S-eliprodil. Laser burn lesion areas in S-eliprodil (20 mg/kg) dosed rats averaged 43,098.5 $\mu^2$ (SEM= 2992.94 $\mu^2$). Lesion area was 15% smaller than lesion areas in vehicle dosed rats but were not significantly different than vehicle controls (FIG. 3).

SUMMARY

Both the R-isomer and the racemic mixture of eliprodil provided significant reduction of collateral retinal damage around the laser burn. Eliprodil (racemic) was found to be two fold more potent and twice as efficacious in this laser burn spread model compared to R-eliprodil. Both of these molecules have nanomolar binding affinities to the NMDA receptor, compared to S-eliprodil, which was devoid of significant efficacy in this model and has millimolar affinity to the NMDA receptor.

The following formulations are representative and not limiting.

EXAMPLE 3

| 1.0% Eliprodil Suspension w/v % | |
|---|---|
| Eliprodil | 1% |
| Hydroxypropyl methylcellulose | 0.5% |
| Dibasic sodium phosphate (anhydrous) | 0.2% |
| Sodium chloride | 0.75% |
| Disodium EDTA (edetate disodium) | 0.01% |
| Polysorbate 80 | 0.05% |
| Benzalkonium chloride solution | 0.01% + 5% xs |
| Sodium hydroxide | adjust to pH 5 |
| Hydrochloric acid | adjust to pH 5 |
| Water for injection | q.s. to 100% |
| Target Tonicity = 290 mOsm/Kg | Target pH = 5 |

EXAMPLE 4

| 3.0% Eliprodil Suspension w/v % | |
|---|---|
| Eliprodil | 3.3% |
| Sodium chloride | 0.9% |
| Polysorbate 80 | 0.1% |
| Water for injection | q.s. to 100% |

EXAMPLE 5

| 10 mM IV Solution w/v % | |
|---|---|
| Glutamate antagonist | 0.384% |
| L-Tartaric acid | 2.31% |
| Sodium hydroxide | pH 3.8 |
| Hydrochloric acid | pH 3.8 |
| Purified water | q.s. 100% |

EXAMPLE 6

| 0.3% Solution w/v % | |
|---|---|
| Glutamate antagonist | 0.33% |
| Sodium acetate | 0.07% |
| Mannitol | 4.3% |
| Disodium EDTA (edetate disodium) | 0.1% |
| Benzalkonium chloride solution | 0.01% |
| Sodium hydroxide | pH 4.0 |
| Hydrochloric acid | pH 4.0 |
| Purified water | q.s. 100% |

EXAMPLE 7

| R-Eliprodil 5 mg Capsules | | |
|---|---|---|
| Ingredient | mg/capsule (Total Wt. 221 mg) | % w/w |
| R-Eliprodil hydrochloride | 5.53[1] | 2.5% |
| Lactose | 206.67 | 93.52% |
| Sodium starch glycolate | 6.6 | 2.98% |
| Magnesium stearate | 2.2 | 1.00% |

[1] Equivalent to 5 mg Eliprodil as free base.

EXAMPLE 8

| Ingredient | mg/capsule (Total Wt. 221 mg) | % w/w |
|---|---|---|
| S-Eliprodil 50 mg Capsules | | |
| S-Eliprodil hydrochloride | 55.25[1] | 25% |
| Lactose (monohydrate) | 156.95 | 71.02% |
| Sodium starch glycolate | 6.6 | 2.98% |
| Magnesium stearate | 2.2 | 1.00% |

[1]Equivalent to 50 mg Eliprodil as free base.

EXAMPLE 9

| Ingredient | mg/capsule (Total Wt. 221 mg) | % w/w |
|---|---|---|
| R-Eliprodil 10 mg Capsules | | |
| R-Eliprodil hydrochloride | 11.05[1] | 5% |
| Lactose (monohydrate) | 201.15 | 91.02% |
| Sodium starch glycolate | 6.6 | 2.98% |
| Magnesium stearate | 2.2 | 1.00% |

[1]Equivalent to 10 mg Eliprodil as free base.

EXAMPLE 10

| Ingredient | mg/capsule (Total Wt. 221 mg) | % w/w |
|---|---|---|
| Eliprodil 20 mg Capsules | | |
| Eliprodil hydrochloride | 22.1[1] | 10% |
| Lactose | 190.1 | 86.02% |
| Sodium starch glycolate | 6.6 | 2.98% |
| Magnesium stearate | 2.2 | 1.00% |

[1]Equivalent to 20 mg Eliprodil as free base.

We claim:

1. A method for treating disorders of the outer retina which comprises administering a pharmaceutically effective amount of a glutamate antagonist.

2. The method of claim 1 wherein the glutamate antagonist is a polyamine site antagonist.

3. The method of claim 1 wherein the glutamate antagonist is a compound of the formula:

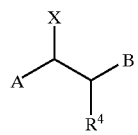

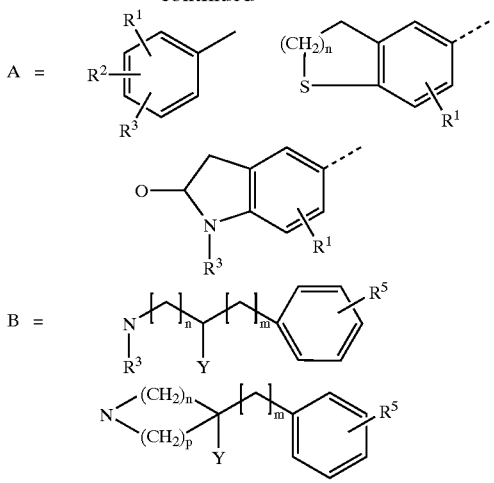

$Y, X = OH, H$ $m = 0-3$ $n, p = 1, 2$ $R^1$=H, halogen, trifluoromethyl, C1–4 alkyl, OH, C1–4 alkoxy, benzyloxy, C1–16 alkanoyloxy, benzoyloxy or when $R^2$=OH or methoxy in the 4-positionl and $R^3$=H then $R^1$=hyroxymethyl, carbamoyl, or C1–4 alkoxycarbonyl;

$R^2$=H, halogen, C1–4 alkyl, OH, C1–4 alkoxyl;

$R^3$, $R^4$=H, C1–4 alkyl; and $R^5$=H, halogen, trifluoromethyl, C1–4 alkyl, OH, C1–4 alkoxy, benzyloxy, C1–16 alkanoyloxy, benzoyloxy, in a pharmaceutically acceptable carrier.

4. The method of claim 3 wherein the compound is eliprodil.

5. The method of claim 4 wherein the compound is R or S eliprodil.

6. The method of claim 1 wherein the disorder is selected from the group consisting of: age-related macular degeneration; retinitis pigmentosa and other forms of heredodegenerative retinal disease; retinal detachment and tears; macular pucker; ischemia affecting the outer retina; damage associated with laser therapy (grid, focal and panretinal) including photodynamic therapy (PDT); trauma; surgical (retinal translocation, subretinal surgery or vitrectomy) or light induced iatrogenic retinopathy; and preservation of retinal transplants.

7. The method of claim 6 wherein the compound is eliprodil or its R or S isomer.

* * * * *